United States Patent
Ying

(10) Patent No.: US 9,076,563 B2
(45) Date of Patent: Jul. 7, 2015

(54) ANTI-SCATTER COLLIMATORS FOR DETECTOR SYSTEMS OF MULTI-SLICE X-RAY COMPUTED TOMOGRAPHY SYSTEMS

(71) Applicant: Zhengrong Ying, Belmont, MA (US)

(72) Inventor: Zhengrong Ying, Belmont, MA (US)

( * ) Notice: Subject to any disclaimer, the term of this patent is extended or adjusted under 35 U.S.C. 154(b) by 210 days.

(21) Appl. No.: 13/908,897

(22) Filed: Jun. 3, 2013

(65) Prior Publication Data

US 2014/0355734 A1    Dec. 4, 2014

(51) Int. Cl.
*A61B 6/03* (2006.01)
*G21K 1/02* (2006.01)
*G01T 1/164* (2006.01)
*A61B 6/00* (2006.01)

(52) U.S. Cl.
CPC .............. *G21K 1/025* (2013.01); *G01T 1/1648* (2013.01); *A61B 6/032* (2013.01); *A61B 6/4291* (2013.01)

(58) Field of Classification Search
CPC ............ A61B 6/03; A61B 6/035; G21K 1/02; G21K 1/025
See application file for complete search history.

(56) References Cited

U.S. PATENT DOCUMENTS

| | | | |
|---|---|---|---|
| 6,215,843 B1 * | 4/2001 | Saito et al. | 378/19 |
| 6,687,333 B2 * | 2/2004 | Carroll et al. | 378/119 |
| 6,733,266 B1 | 5/2004 | Guida | |
| 6,778,637 B2 | 8/2004 | Luhta | |
| 6,934,354 B2 | 8/2005 | Hoffman | |
| 7,027,553 B2 * | 4/2006 | Dunham et al. | 378/5 |
| 7,564,940 B2 | 7/2009 | Mattson | |
| 7,590,215 B2 * | 9/2009 | Schlomka | 378/4 |
| 7,734,017 B2 | 6/2010 | Zeitler | |
| 8,262,288 B2 | 9/2012 | Shaughnessy | |
| 2003/0076929 A1 * | 4/2003 | Hoheisel et al. | 378/98.8 |
| 2004/0208277 A1 * | 10/2004 | Morikawa et al. | 378/4 |
| 2007/0019779 A1 * | 1/2007 | Nishide et al. | 378/4 |
| 2007/0025518 A1 * | 2/2007 | Levene et al. | 378/149 |
| 2009/0225953 A1 * | 9/2009 | Danzer | 378/147 |
| 2010/0163738 A1 * | 7/2010 | Danzer et al. | 250/366 |
| 2010/0189211 A1 * | 7/2010 | Behling | 378/4 |
| 2011/0075804 A1 * | 3/2011 | Boese et al. | 378/62 |
| 2012/0069954 A1 * | 3/2012 | Iso et al. | 378/7 |
| 2012/0300907 A1 * | 11/2012 | Wirth | 378/154 |
| 2013/0163715 A1 * | 6/2013 | Kurochi | 378/19 |
| 2013/0168567 A1 * | 7/2013 | Wartski et al. | 250/394 |

\* cited by examiner

*Primary Examiner* — Charlie Y Peng

(57) ABSTRACT

A detector system for multi-slice X-ray Computed Tomography (CT) system is disclosed. The detector system comprises a plurality of X-ray detector modules for detecting X-ray photons; wherein each detector module is divided into individual detector elements organized in a matrix fashion with element rows (z-axis for row direction) and element columns (x-axis for column direction) for detecting X-ray photons; wherein the individual detector elements are interspaced by gaps (areas that do not detect radiation), which are also organized in a matrix fashion with gap rows and gap columns; and an anti-scatter collimator comprising a plurality of anti-scatter plates, which is placed above the detector modules and aligned to focus on an X-ray source of the CT system; wherein some or all of the anti-scatter plates are placed above the detector elements; wherein those anti-scatter plates that are placed above the detector elements block a portion of primary X-ray photons from the X-ray source in addition to scattered X-ray photons from reaching the detector elements.

11 Claims, 8 Drawing Sheets

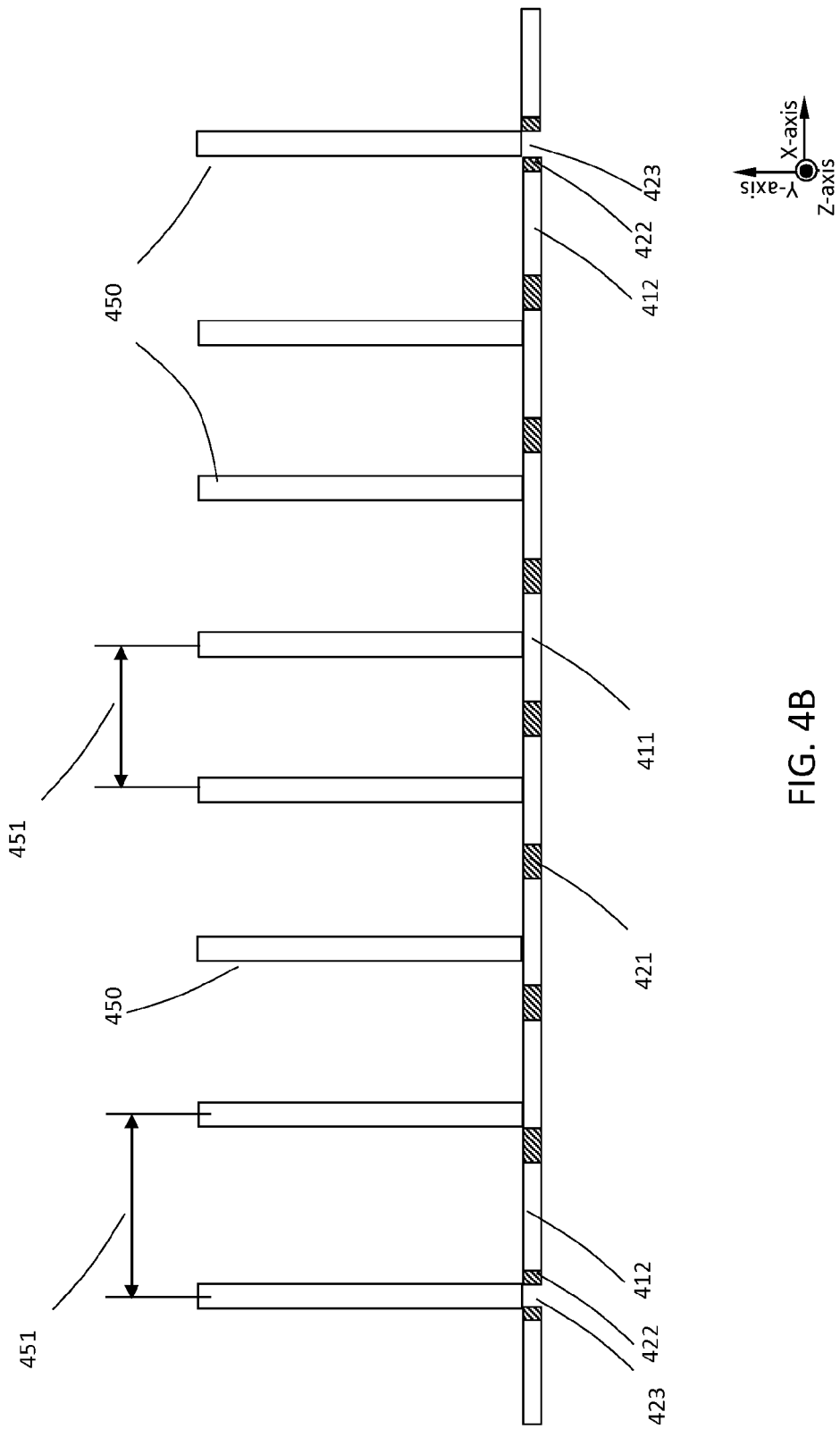

ANTI-SCATTER COLLIMATORS FOR DETECTOR SYSTEMS OF MULTI-SLICE X-RAY COMPUTED TOMOGRAPHY SYSTEMS

RELATED APPLICATIONS

This patent application is related to the following pending U.S. applications and/or issued U.S. patents, the contents of which are incorporated herein in their entirety by reference:

"Configurable data measurement and acquisition systems for multi-slice x-ray computed tomography systems," invented by Zhengrong Ying, U.S. application Ser. No. 13/589,245, filed on Aug. 20, 2012.

"Adjustable photon detection systems for multi-slice x-ray computed tomography systems," invented by Zhengrong Ying, U.S. application Ser. No. 13/760,127, filed on Feb. 6, 2013.

FIELD OF THE DISCLOSURE

The present disclosure relates to multi-slice X-ray Computed Tomography (CT) systems.

BACKGROUND

In X-ray CT systems, X-rays are used to image internal structures and features of a region of a subject or an object. The terms "subject" and "object" shall include anything capable of being imaged. The imaging is performed by an X-ray CT system, which images internal structures and features of a plurality of thin planar slices or a 3D volume of a region of an object using X-rays. For medical applications, the imaging objects include human bodies.

An X-ray CT system generally comprises an X-ray source that provides a cone-shaped X-ray beam and an array of closely spaced X-ray detectors that face the X-ray source. The X-ray source and the array of detectors are mounted in a gantry so that a patient being imaged with the CT system, generally lying on an appropriate support couch, can be positioned within the gantry between the X-ray source and the array of detectors. The gantry and the couch are moveable relative to each other so that the X-ray source and the detector array can be positioned axially at desired locations along the patient's body.

The gantry comprises a stationary structure referred to as a stator and a rotary element referred to as a rotor, which is mounted to the stator so that the rotor is rotatable about the axial direction. In third generation CT systems, the X-ray source and the array of detectors are mounted on the rotor. Angular positions of the rotor about the axial direction are controllable so that the X-ray source can be positioned at desired angles, referred to as view angles, around a patient's body.

To image a slice in a region of a patient's body, the X-ray source is positioned at an axial position of the slice and the X-ray source is rotated around the slice to illuminate the slice with X-rays from a plurality of different view angles. At each view angle, detectors in the array of detectors generate signals responsive to the intensity of X-rays from the source that pass through the slice. The signals are processed to determine the amounts, by which X-rays from the X-ray source are attenuated over various path lengths through the slice that the X-rays traverse, in passing though the slice from the X-ray source to the detectors. The amounts, by which the X-rays are attenuated, are used to determine the X-ray absorption coefficients of materials in the slice as a function of position in the slice. The absorption coefficients are used to generate an image of the slice and identify compositions and densities of tissues in the slice.

The X-ray detectors comprised in a detector array of CT system are generally packaged in a plurality of modules, hereinafter referred to as detector modules, each of which comprises a plurality of X-ray detector elements. Most modern CT systems are multi-slice CT systems designed to simultaneously image a plurality of slices of a patient. The X-ray detector elements in each detector module of a multi-slice CT scanner are arranged in a matrix of rows and columns. The X-ray detector matrices of any two CT detector modules in a CT system are substantially identical and comprise a same number of rows of detector elements and a same number of columns of detector elements. The modules are positioned one adjacent to and contiguous with the other in a closely packed array with their rows of detectors aligned end to end so that the X-ray detector elements form a plurality of long parallel rows of X-ray detector elements.

A multi-slice X-ray CT system is usually named or featured by the maximum number of slices that it can simultaneously image, for example, an 8-slice CT system means that it can simultaneously image at most 8 slices; a 16-slice CT system can simultaneously image at most 16 slices.

The X-ray detector elements in each long row of the detector array lie on an arc of a circle having its center located at a focal point of the CT system's X-ray source, and the design of these detector elements and the detector modules is specifically determined by the radius of the circle, which is hereinafter referred to as focusing distance. The design of X-ray detector modules placed on the arc of one focusing distance of one CT system cannot therefore be used on another CT system of a different focusing distance.

Each detector element in a scintillator array is comprised of a finite active area for detecting X-ray photons and generating second-energy photons or electric charges when using X-ray direct conversion materials. Detector elements are surrounded by non-active areas, referred hereafter as gaps, which do not generate responses for X-ray photons.

An X-ray detector array typically includes an anti-scatter collimator having a plurality of anti-scatter plates for collimating x-ray beams received at each detector element: a scintillator for converting x-rays to light energy adjacent to the collimator, and a photodiode for receiving the light energy from the coupled scintillator and producing electric charges therefrom. The anti-scatter plates of the collimator are placed at the locations of the gaps of the detector modules to very tight and exact tolerances. This alignment of the detector modules with the anti-scatter plates of the collimator can be very costly for manufacturing because of required very tight and exact tolerances.

SUMMARY OF THE DISCLOSURE

In accordance with one embodiment of the present disclosure, a detector system for a multi-slice X-ray Computed Tomography (CT) system, wherein the multi-slice X-ray CT system comprises at least one X-ray source, comprises: a plurality of X-ray detector modules for detecting X-ray photons; wherein each of the detector modules is divided into individual detector elements organized in a matrix fashion with element rows (z-axis for row direction) and element columns (x-axis for column direction) for detecting X-ray photons; wherein the individual detector elements are inter-spaced by gaps (areas that do not detect radiation), which are also organized in a matrix fashion with gap rows and gap columns; and an anti-scatter collimator comprising a plurality of anti-scatter plates placed above the detector modules and aligned to focus on the X-ray source; wherein some or all of the anti-scatter plates are placed above the detector elements; wherein those anti-scatter plates that are placed above the detector elements block a portion of primary X-ray photons from the X-ray source in addition to scattered X-ray photons from reaching the detector elements.

In accordance with one aspect of the embodiment of the present disclosure, the anti-scatter plates parallel with the z-axis may be placed above some or all element columns of the detector modules but not above any gap columns of the detector modules; the anti-scatter plates parallel with the z-axis may not be placed between any of two detector modules next to each other along the x-axis.

In accordance with another aspect of the embodiment of the present disclosure, the anti-scatter plates parallel with the z-axis may be placed above some or all element columns of the detector modules but not above any middle gap columns of the detector modules; wherein the anti-scatter plates parallel with the z-axis may also be placed between any of two detector modules next to each other along the x-axis.

In accordance with yet another aspect of the embodiment of the present disclosure, the edge element column width of the detector modules may be smaller than the middle element column width of the detector modules. There may be one anti-scatter plate placed above each middle element column of the detector module; wherein no anti-scatter plates may be placed above the two edge element columns of the detector modules; wherein one anti-scatter plate may be placed between two detector modules next to each other along the x-axis. The nominal value of the thickness of the anti-scatter plates may equal to the difference between the edge element column width and the middle element column width of the detector modules.

In accordance with another embodiment of the present disclosure, a multi-slice X-ray Computed Tomography (CT) system for generating CT images for objects to be imaged comprises: a rotatable gantry; an X-ray source mounted on the rotatable gantry for generating X-ray beams to pass through the objects; and a detector system mounted on the rotatable gantry to the opposite side of the X-ray source, for receiving the X-ray beams corresponding to the objects. The detector system comprises: a plurality of X-ray detector modules for detecting X-ray photons; wherein each detector module is divided into individual detector elements organized in a matrix fashion with element rows (z-axis for row direction) and element columns (x-axis for column direction) for detecting X-ray photons; wherein individual detector elements are interspaced by gaps (areas that do not detect radiation), which are also organized in matrix fashion with gap rows and gap columns; and an anti-scatter collimator comprising a plurality of anti-scatter plates, which is placed above the detector modules and aligned to focus on the X-ray source; wherein some or all of the anti-scatter plates are placed above the detector elements; wherein those anti-scatter plates that are placed above the detector elements block a portion of primary X-ray photons from the X-ray source in addition to scattered X-ray photons from reaching the detector elements.

BRIEF DESCRIPTION OF THE DRAWINGS

The drawing figures depict embodiments by way of example, not by way of limitation. In the figures, like reference numerals refer to the same or similar elements.

FIG. 4B shows a cross-sectional view illustrating an arrangement of anti-scatter plates of an anti-scatter collimator and detector modules of a CT detector system in accordance with one embodiment of the present disclosure.

DETAILED DESCRIPTION OF THE DRAWINGS

Figure 1:
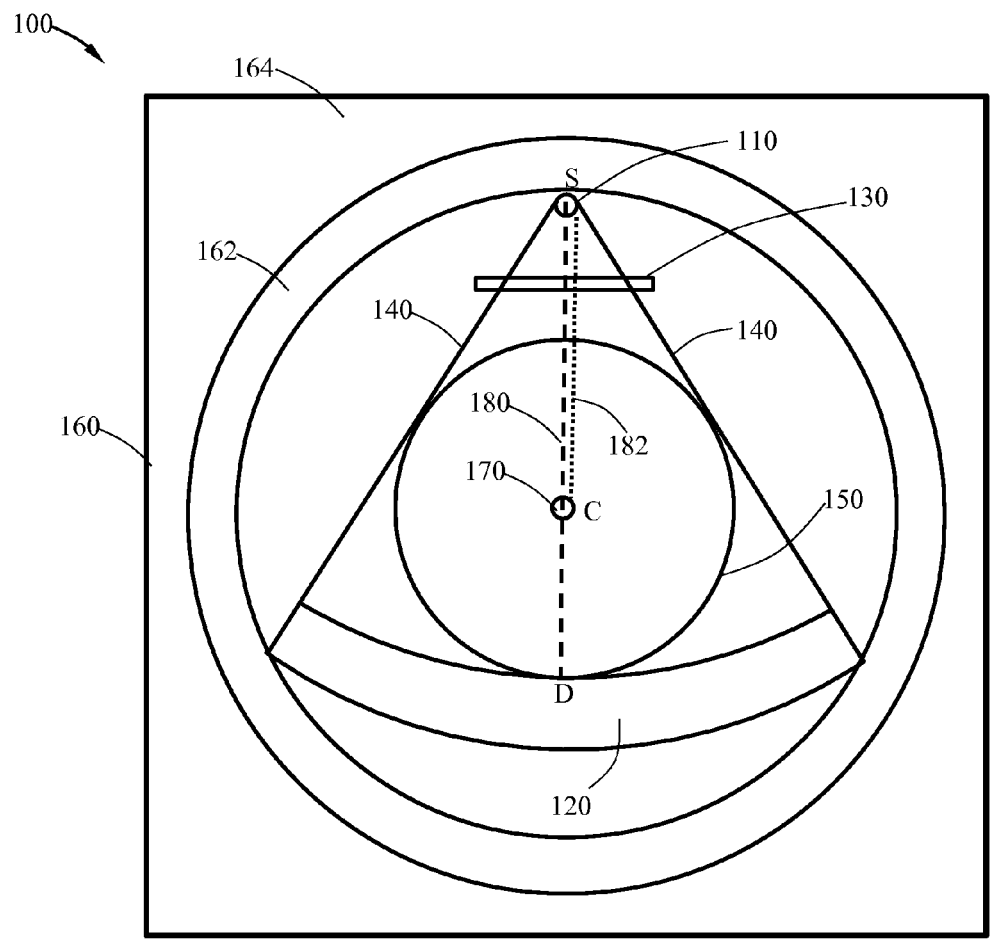
FIG. 1 illustrates a schematic functional diagram of a prior art multi-slice X-ray CT system.
Figure 1:
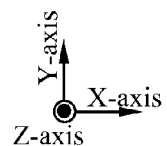

FIG. 1 shows a schematic functional diagram of a prior art multi-slice X-ray CT system 100. A multi-slice CT system typically comprises an X-ray source 110, which generates a cone-shaped X-ray beam 140. The X-ray beam 140 passes through a pre-patient collimator 130, which allows X-ray beam to illuminate only the targeted area and blocks X-ray beam in unwanted area. A patient usually lies down within the scanner's scanning Field Of View (FOV) 150, where the X-ray beam 140 illuminates. The X-ray detector system 120 receives X-ray photons and converts to analog signals that are proportional to X-ray photon energies. The X-ray CT system 100 also comprises a gantry 160, which includes a rotational part 162 and a stationary part 164. The X-ray source 110, the collimator 130 and the detector system 120 are mounted on the rotational part 162 of the gantry 160. The rotational part 162 rotates around the rotation center C 170.

The distance 182 between the focal spot S, which sometimes is interchangeably referred to as X-ray source position, of the X-ray source 110 and the rotation center C, which is interchangeably called iso-center, is hereinafter referred to as $R_{sc}$, and the distance 180 between the focal spot S of the X-ray source 110 and the detector system D is hereinafter referred to as focusing distance $R_{sd}$. Different CT systems may have different $R_{sc}$, $R_{sd}$, or/and scanning FOV.

The direction from the iso-center to the focal spot of the X-ray source is hereinafter referred to as y-axis, and the direction perpendicular to the imaging plane or the rotation plane is hereinafter referred to as z-axis, and the direction perpendicular to the y-axis within the rotation plane is hereinafter referred to as x-axis.

Figure 2A:
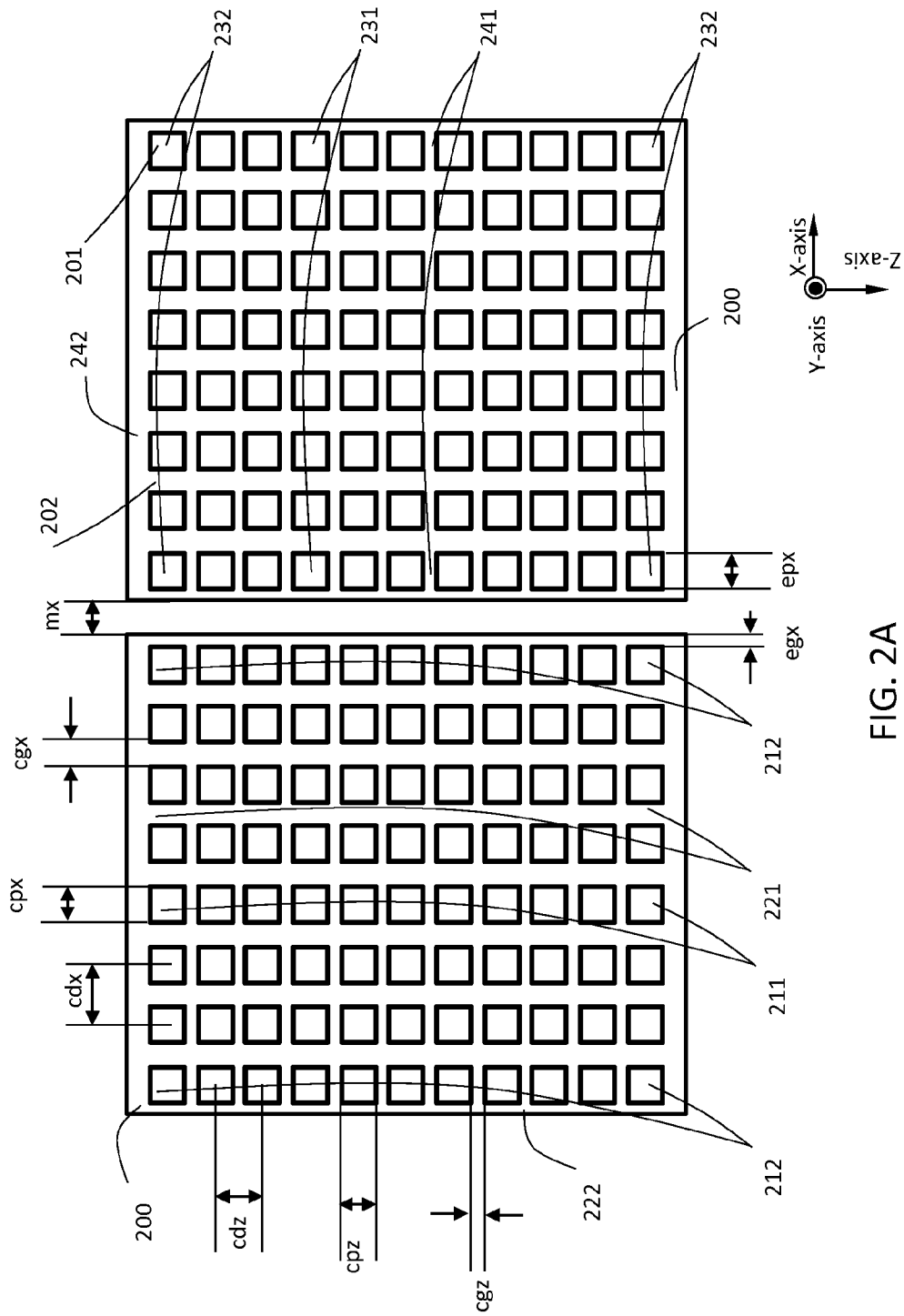
FIG. 2A illustrates prior art detector modules placed side by side to form a CT detector system.

FIG. 2A illustrates prior art detector modules placed side by side to form a CT detector system. A CT detector system is comprised of many detector modules 200 placed side by side along an arced support structure. Each detector module is divided into individual detector elements 201 in a matrix fashion with rows and columns. The row direction is along the z-axis and the column direction is along the x-axis. An element column 211 or 212 is defined as a plurality of detector elements along the z-axis at a given column position (position along the x-axis); and an element row 231 or 232 is defined as a plurality of detector elements along the x-axis at a given row position (position along the z-axis). Edge element columns 212 of a detector module are the two element columns next to the edges of a detector module, and middle element columns 211 of a detector module are all the element columns except the edge element columns of a detector module. Edge element rows 232 of a detector module are the two element rows next to the edges of a detector module, and middle element rows 231 of a detector module are all the element rows except the edge element rows of a detector module.

Each detector element 201 receives X-ray photons and converts into second energy light photons when using scintillating material; or directly into electric charges when using direct conversion materials such as CZT (Cadmium Zinc Telluride). The individual detector elements 201 are interspaced by gaps 202 that do not detect X-ray photons usually are filled with high-Z materials or masks for blocking X-ray photons. The gaps 202 are also formed in a matrix fashion with rows and columns. A middle gap column 221 is defined as the gap between two element columns, an edge gap column 222 is between a detector module edge parallel to the z-axis and an edge element column; middle gap columns and/or edge gap columns are referred to hereafter as gap columns. A middle gap row 241 is defined as the gap between two element rows of a detector module; an edge gap row 242 is between a detector module edge parallel to the x-axis and an edge element row of a detector module; middle gap rows and/or edge gap rows are referred to hereafter as gap rows.

For a detector module, the distances between the centers of two neighboring detector elements are referred to as pitch. The pitch along the x-axis is denoted by cdx, and the pitch along the z-axis is denoted by cdz. The dimensions of each individual detector are denoted by cpx along the x-axis (element column width) and cpz along the z-axis (element row height) respectively. The dimensions of the gaps are denoted by cgx along the x-axis (gap column width) and cgz along the z-axis (gap row height). The edge column gap width is denoted by egx.

The distance between two neighboring modules is denoted by mx. For the reasons that will be described later in this specification, the element column width of the two edge element columns may be different from that of the middle element columns; the edge element column width is denoted by epx.

An example of the dimensions of a detector module of 32 element rows by 24 element columns with same element column width is as follows: cdx=1 mm; epx=cpx=0.85 mm; cgx=0.15 mm; egx=0.085 mm; cdz=1 mm; cpz=0.915 mm; cgz=0.085 mm.

An example of the dimensions of a detector module of 32 element rows by 24 element columns with the edge element column width different from the middle element column width is as follows: cdx=1 mm; cpx=0.915 mm; cgx=0.085 mm; egx=0.085 mm; epx=0.8 mm; cdz=1 mm; cpz=0.915 mm; cgz=0.085 mm.

The detector pitches cdx and cdz determine the spatial resolution of a CT system, such as MTF (Modulation Transfer Function) and SSP (Slice Sensitivity Profile). Given specific detector pitches, it is important to have the gap column width cgx and the gap row height cgz as small as possible (or have the element column width cpx and the element row height cpz as large as possible) so that each individual detector element receives as much X-ray photons as possible to have enough SNR (signal to noise ratio) in the reconstructed images to be used for diagnosis, thus reducing the radiation dose to patients.

Because of the mechanical tolerances of the detector modules and constraints in assembling the detector modules, module to module spacing may be needed. An example of the module to module spacing mx=0.1 mm.

For the detector modules with the same element column width, the detector pitch between the two neighboring edge element columns of two neighboring detector modules may be different from the detector pitch within the detector module because of added module to module spacing.

By reducing the edge element column width (thus the edge element column width is smaller than the middle element column width), the detector pitch between the two neighboring edge element columns of the two neighboring detector modules may be maintained the same as the detector pitch within the detector module.

Figure 2B:
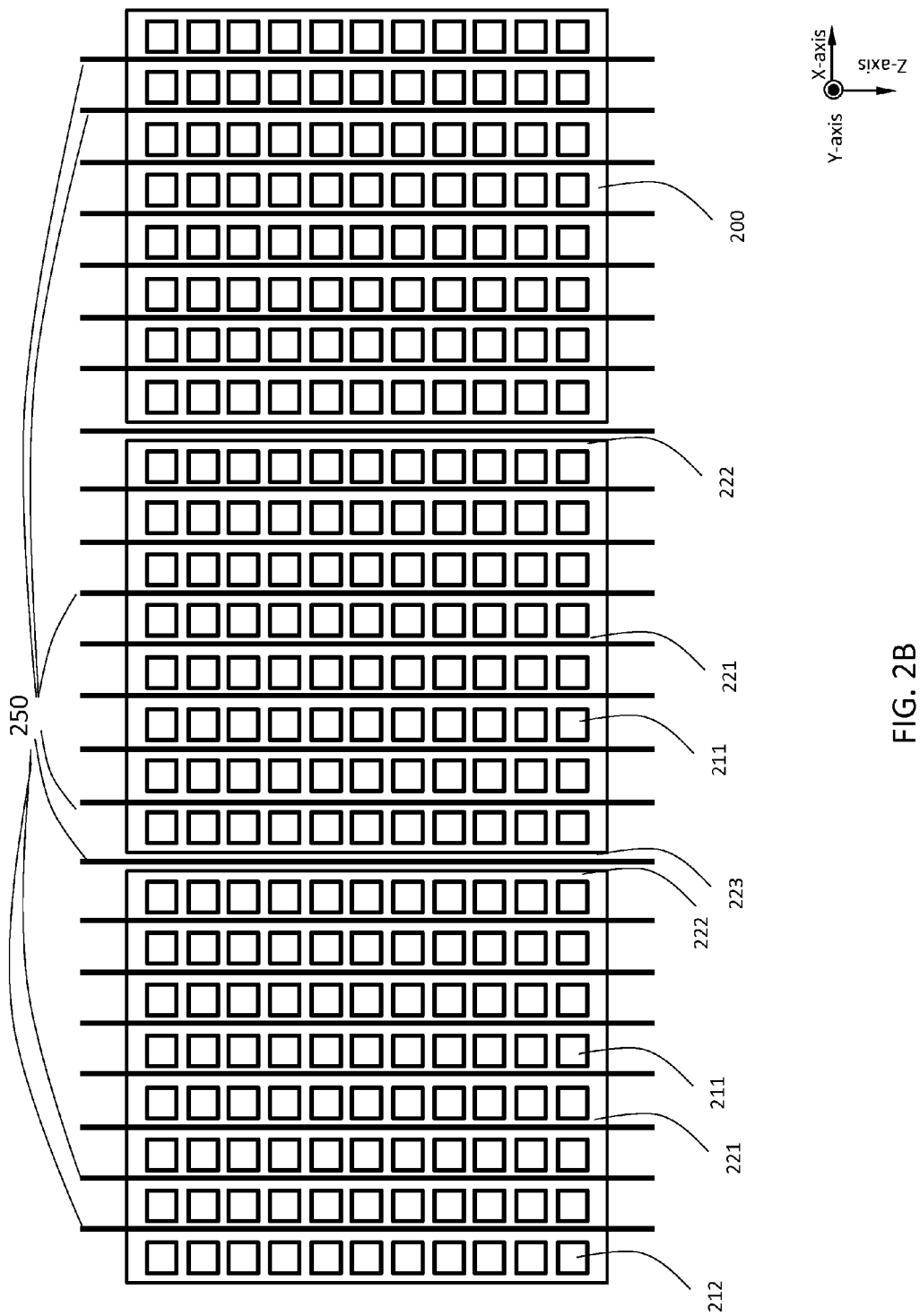
FIG. 2B illustrates a prior art arrangement of anti-scatter plates and detector modules of a CT detector system.
Figure 2C:
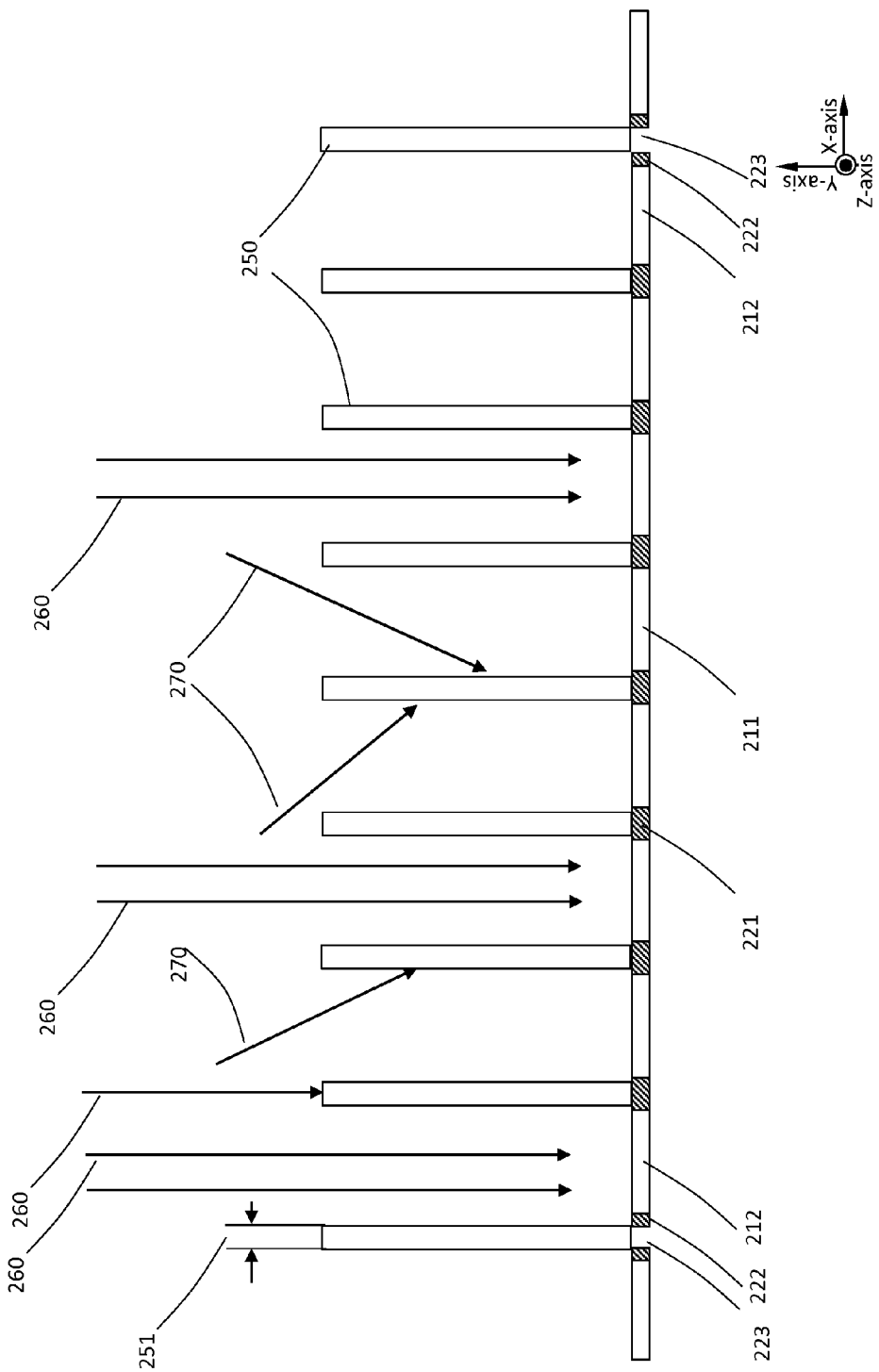
FIG. 2C shows a cross-sectional view illustrating a prior art arrangement of anti-scatter plates and detector modules of a CT detector system.

FIG. 2B illustrates a prior art arrangement of anti-scatter plates of an anti-scatter collimator and detector modules of a CT detector system. FIG. 2C shows a cross-sectional view illustrating a prior art arrangement of anti-scatter plates of an anti-scatter collimator and detector modules of a CT detector system. The anti-scatter plates 250 parallel with the z-axis are placed above detector modules, and are aligned to focus on an X-ray source of a CT system. The anti-scatter plates 250 are placed above the gap columns 221 and 222 of the detector modules and the spacing 223 between two neighboring detector modules; the anti-scatter plates 250 are not placed above the middle element columns 221 or the edge element columns 222. The thickness 251 of the anti-scatter plates is smaller than the column gap width cgx as well as the gap between two neighboring modules 2egx+mx, so that the anti-scatter plates do not block primary X-ray photons 260 from reaching the individual detector elements. The primary X-ray photons 260 are the X-ray photons emitted from the X-ray source; these primary X-ray photons 260 have been attenuated if there are scanned objects or patients along the path. The scattered X-ray photons (or scatters) 270 are the X-ray photons generated by the interaction of primary X-ray photons with scanned objects or patients; and the directions of the scatters are typically uniformly distributed around an interaction point. Therefore placing the anti-scatter plates aligned to focus on the X-ray source above the detector modules reduces the amount of scatters from reaching the individual detector elements, improving the primary to scatter ratio.

When the anti-scatter plates 250 are placed above the gap columns (221 and 222) of the detector modules 200, the thickness of the anti-scatter plates is, for example, constrained to be smaller than the gap column width so that the anti-scatter plates do not block the primary photons from reaching the detector elements, resulting in very tight tolerance requirement on the thickness of the anti-scatter plates as well as the high precision and tight tolerance requirements on the placement locations for the anti-scatter plates; such tight tolerance and high precision requirements make the manufacturing and assembly of a CT detector system very costly.

Figure 3A:
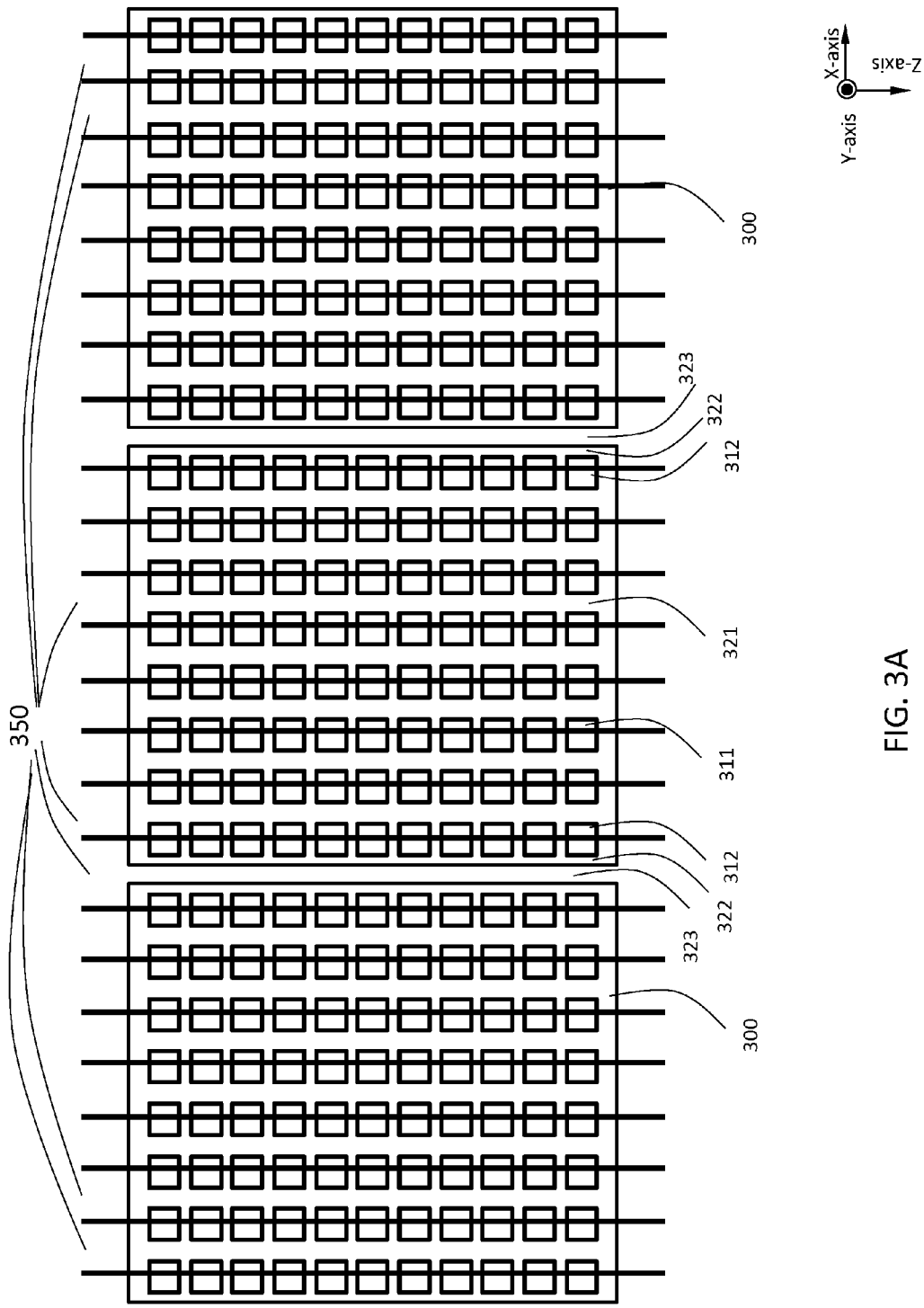
FIG. 3A illustrates an arrangement of anti-scatter plates of an anti-scatter collimator and detector modules of a CT detector system in accordance with one embodiment of the present disclosure.
Figure 3B:
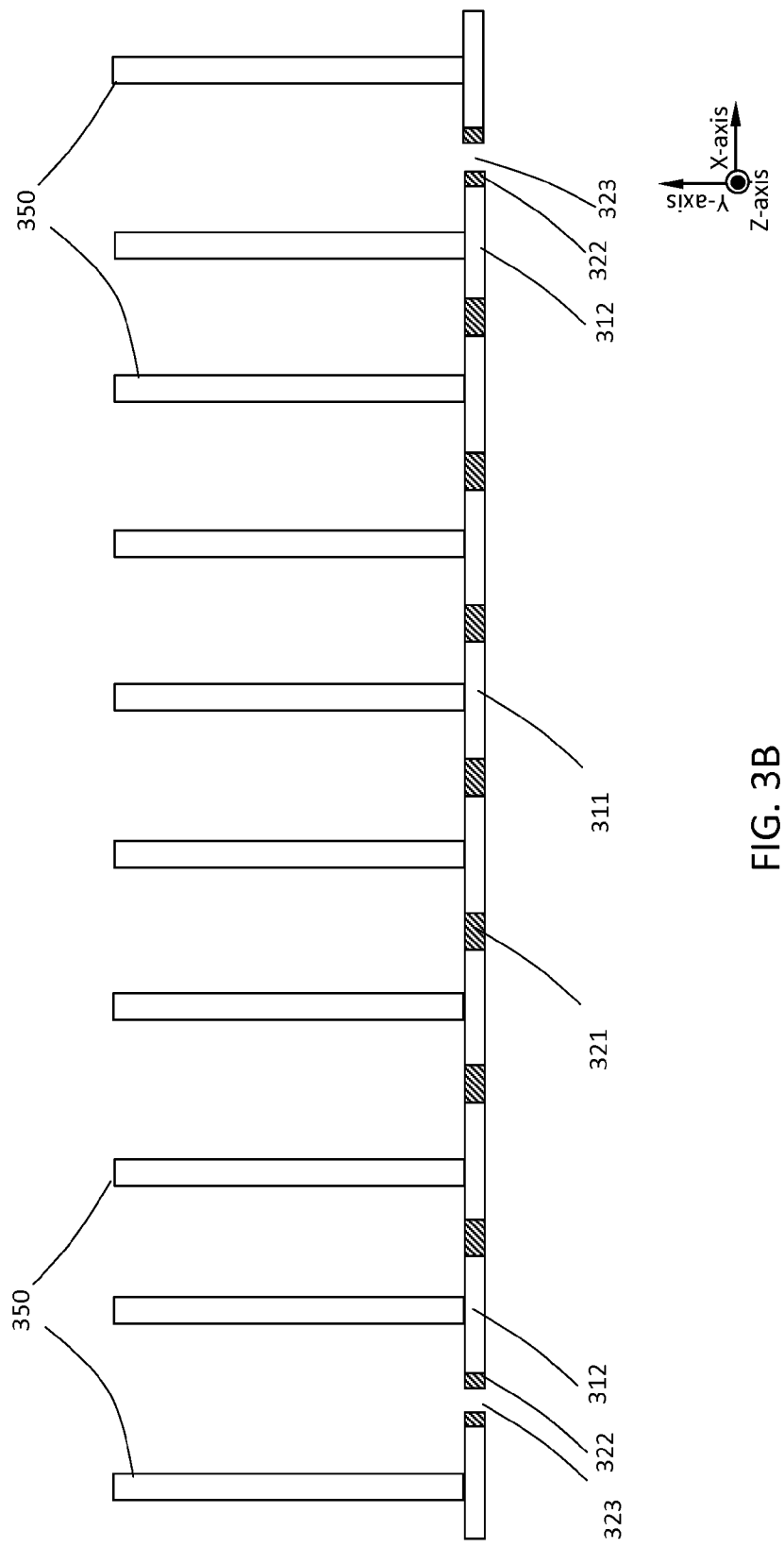
FIG. 3B shows a cross-sectional view illustrating an arrangement of anti-scatter plates of an anti-scatter collimator and detector modules of a CT detector system in accordance with one embodiment of the present disclosure.

FIG. 3A illustrates an arrangement of anti-scatter plates of an anti-scatter collimator and detector modules of a CT detector system in accordance with one embodiment of the present disclosure. FIG. 3B shows a cross-sectional view illustrating an arrangement of anti-scatter plates of an anti-scatter collimator and detector modules of a CT detector system in accordance with one embodiment of the present disclosure.

In accordance with one embodiment of the present disclosure, anti-scatter plates 350 are placed above the element columns 311 and 312 of the detector modules 300 instead of gap columns 321 and 322 of the detector modules 300. Since the element column width is much larger than the gap column width, the precision and tolerance requirements for placing the anti-scatter plates can be reduced, thus lowering the manufacturing and assembly cost for the CT detector systems.

Since the anti-scatter plates 350 are placed directly above the element columns 311 and 312, some primary photons are blocked by the anti-scatter plates from reaching the detector elements. The effective element column width is the difference between the element column width and the thickness of the anti-scatter plates, or the effective gap column width is the sum of the gap column width and the thickness of the anti-scatter plates. In accordance with one aspect of the embodiment of the present disclosure, the gap column width of the detector module can be reduced, for example, to 50 um, because of no need to accommodate the thickness of the anti-scatter plates to be within the gap column.

In another aspect of the embodiment, the detector modules have substantially same element column width for all the element columns; each anti-scatter plate 350 is placed above the center of each element column 311 or 312; no anti-scatter plates are placed above the gap columns 321 or 322 of the detector modules or above the spacing 323 between the two neighboring detector modules 300 along the x-axis. For example, a detector system comprises 37 detector modules with each detector module comprising 24 columns by 32 rows of detector elements; detector modules are placed side by side along the arc centered at the X-ray source; anti-scatter plates are aligned to focus on the X-ray source and placed above the center of each element column of each detector module, resulting in 888 (24 columns/module and 37 modules) anti-scatter plates 350 for an entire detector system.

Figure 4A:
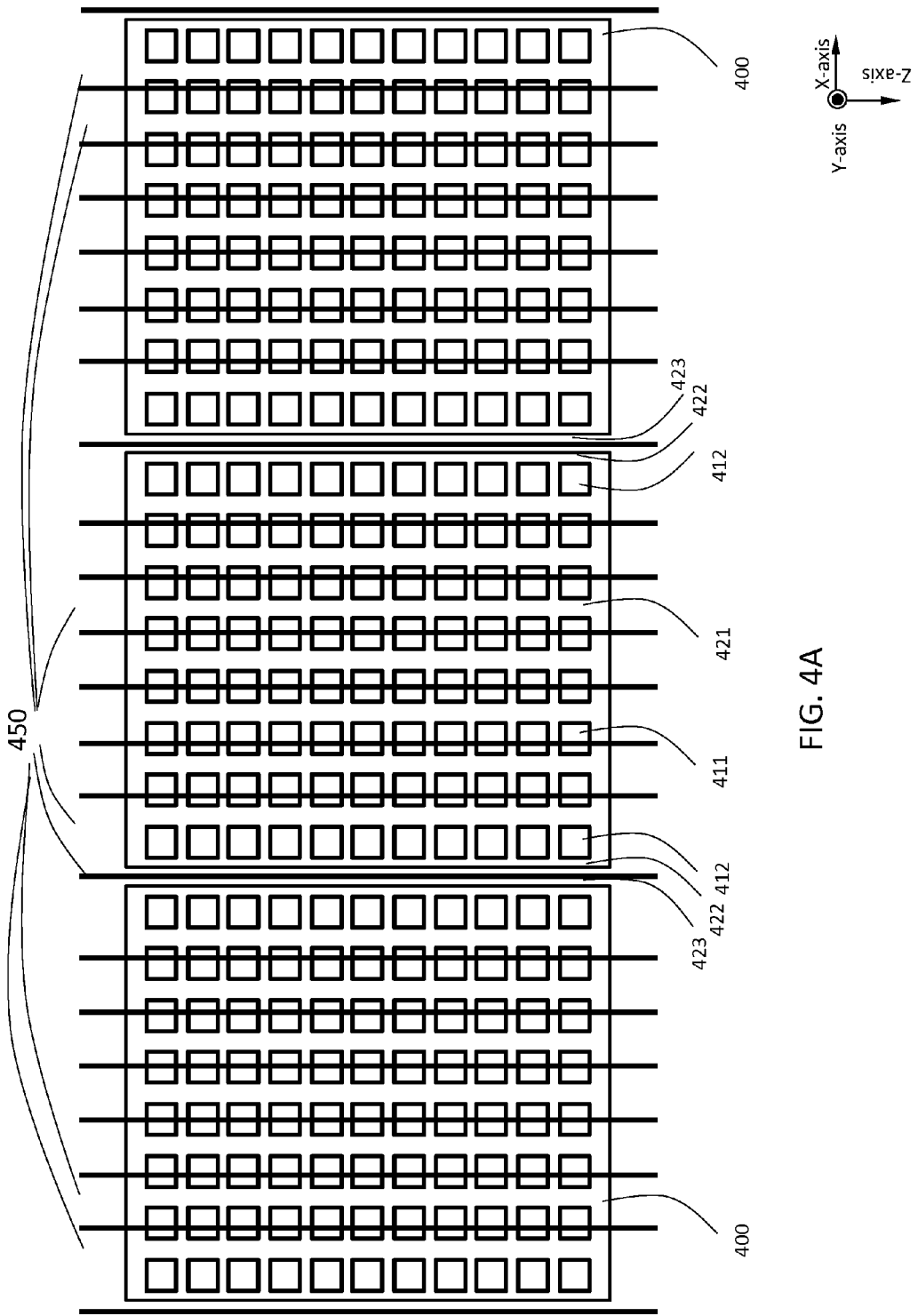
FIG. 4A illustrates an arrangement of anti-scatter plates of an anti-scatter collimator and detector modules of a CT detector system in accordance with one embodiment of the present disclosure.

FIG. 4A illustrates an arrangement of anti-scatter plates of an anti-scatter collimator and detector modules of a CT detector system in accordance with one embodiment of the present disclosure. FIG. 4B shows a cross-sectional view illustrating an arrangement of anti-scatter plates of an anti-scatter collimator and detector modules of a CT detector system in accordance with one embodiment of the present disclosure.

In accordance with one embodiment of the present disclosure, anti-scatter plates 450 are placed above the middle element columns 411 of the detector modules 400 but not on the edge element columns 412; anti-scatter plates 450 are also placed above the spacing 423 between two neighboring detector modules 400. For example, a detector system comprises 37 detector modules with each detector module comprising 24 columns by 32 rows of detector elements; detector modules are placed side by side along the arc centered at the X-ray source; anti-scatter plates are aligned to focus on the X-ray source and placed above the center of each element column of each detector module, resulting in 852 (22 middle element columns/module and 37 modules+38 at module spacing including both ends) anti-scatter plates for an entire detector system.

In one aspect of the embodiment of the present disclosure, the edge element column width of the detector modules 400 is smaller than the middle element column width of the detector modules 400. For example, the edge element column width is 0.80 mm, and the middle element column width is 0.915 mm. In another aspect of the embodiment of the present disclosure, the nominal value of the thickness of the anti-scatter plates 450 may be the difference between the middle element column width and the edge element column width. For example, the nominal value of the thickness of the anti-scatter plates is 0.115 mm for the previous example.

In another aspect of the embodiment of the present disclosure, the anti-scatter plate pitch 451 as shown in FIG. 4B, which is the distance between two neighboring anti-scatter plates, is arranged in a non-decreasing fashion from the center of a detector module to the two edges of the detector module. The anti-scatter plates for each detector module are arranged in the same fashion for the entire anti-scatter collimator of the detector system, resulting in a cyclical function of anti-scatter plate pitch with respect to the fan angle for the entire detector system.

In accordance with another embodiment of the present disclosure, the anti-scatter collimator comprises two dimensional anti-scatter plates placed along the x-axis and along the z-axis. It will be understood by those skilled in the art that the anti-scatter plates parallel with the x-axis may also be placed above the element rows of the detector modules instead of the gap rows of the detector modules to reduce the tolerance and precision requirements for the manufacturing and assembly of the anti-scatter collimators. While this disclosure has been particularly shown and described with references to the embodiments thereof, it will be understood by those skilled in the art that various changes in forms and details may be made therein without departing from the spirit and scope of the disclosure as defined by the following claims.

The invention claimed is:

1. A detector system for a multi-slice X-ray Computed Tomography (CT) system, wherein said X-ray CT system comprises at least one X-ray source, comprising:
   A. A plurality of X-ray detector modules for detecting X-ray photons; wherein each said detector module is divided into individual detector elements organized in a matrix fashion with element rows (z-axis for row direction) and element columns (x-axis for column direction) for detecting X-ray photons; wherein said individual detector elements are interspaced by gaps (areas that do not detect radiation); wherein said gaps are also organized in matrix fashion with gap rows and gap columns; wherein the edge element column width of said detector modules is smaller than the middle element column width of said detector modules; and,
   B. An anti-scatter collimator comprising a plurality of anti-scatter plates placed above said detector modules and aligned to focus on said X-ray source; wherein some or all of said anti-scatter plates are placed above said detector elements; wherein those anti-scatter plates that are placed above said detector elements block a portion of primary X-ray photons from said X-ray source in addition to scattered X-ray photons from reaching said detector elements.

2. The system of claim 1, wherein said anti-scatter plates parallel with the z-axis are placed above some or all element columns of said detector modules and not above any gap columns of said detector modules.

3. The system of claim 2, wherein said anti-scatter plates parallel with the z-axis are not placed between any of two detector modules next to each other along the x-axis.

4. The system of claim 1, wherein said anti-scatter plates parallel with the z-axis are placed above some or all element columns of said detector modules and not above any middle gap columns of said detector modules; wherein said anti-scatter plates parallel with the z-axis are also placed between any of two detector modules next to each other along the x-axis.

5. The system of claim 1, wherein said anti-scatter plates parallel with the x-axis are placed above some or all element rows of said detector modules and not above any gap rows of said detector modules.

6. The system of claim 5, wherein said anti-scatter plates parallel with the x-axis are not placed between any of two detector modules next to each other along the z-axis.

7. The system of claim 1, wherein said anti-scatter plates parallel with the x-axis are placed above some or all element rows of said detector modules and not above any middle gap rows of said detector modules; wherein said anti-scatter plates parallel with the x-axis are also placed between any of two detector modules next to each other along the z-axis.

8. The system of claim 1, wherein there is one said anti-scatter plate placed above each middle element column of said detector module; wherein no anti-scatter plates are placed above said two edge element columns of said detector modules; wherein one said anti-scatter plate is placed between two detector modules next to each other along the x-axis.

9. The system of claim 8, wherein the nominal value of the thickness of said anti-scatter plates may equal to the difference between said edge element column width and said middle element column width of said detector modules.

10. The system of claim 8, wherein the anti-scatter plate pitch is arranged in a non-decreasing fashion from the center to the two edges of each said detector module.

11. A multi-slice X-ray Computed Tomography (CT) system for generating CT images for objects to be imaged comprising:
   A. A rotatable gantry;
   B. An X-ray source mounted on said rotatable gantry for generating X-ray beams to pass through said objects; and
   C. A detector system mounted on said rotatable gantry to the opposite side of said X-ray source, for receiving said X-ray beams corresponding to said objects, comprising:
      i. A plurality of X-ray detector modules for detecting X-ray photons; wherein each said detector module is divided into individual detector elements organized in a matrix fashion with element rows (z-axis for row direction) and element columns (x-axis for column direction) for detecting X-ray photons; wherein said individual detector elements are interspaced by gaps (areas that do not detect radiation); wherein said gaps are also organized in a matrix fashion with gap rows and gap columns; wherein the edge element column width of said detector modules is smaller than the middle element column width of said detector modules; and,
      ii. An anti-scatter collimator comprising a plurality of anti-scatter plates, which is placed above said detector modules and aligned to focus on said X-ray source; wherein some or all of said anti-scatter plates are placed above said detector elements; wherein those anti-scatter plates that are placed above said detector elements block a portion of primary X-ray photons from said X-ray source in addition to scattered X-ray photons from reaching said detector elements.

* * * * *